(12) United States Patent
Amato et al.

(10) Patent No.: US 8,556,988 B2
(45) Date of Patent: Oct. 15, 2013

(54) APPARATUS AND REPAIR OF DEFECT IN INGUINAL CANAL AND OTHER MUSCULAR STRUCTURES

(75) Inventors: Giuseppe Amato, Palermo (IT); Stephen Graham Bell, Rome (IT)

(73) Assignee: Insightra Medical, Inc., Irvine, CA (US)

(*) Notice: Subject to any disclaimer, the term of this patent is extended or adjusted under 35 U.S.C. 154(b) by 1312 days.

(21) Appl. No.: 11/934,897

(22) Filed: Nov. 5, 2007

(65) Prior Publication Data
US 2008/0287970 A1 Nov. 20, 2008

Related U.S. Application Data

(60) Provisional application No. 60/895,039, filed on Mar. 15, 2007.

(51) Int. Cl.
*A61F 2/02* (2006.01)
(52) U.S. Cl.
USPC ...................................... 623/23.72
(58) Field of Classification Search
USPC ............. 606/108, 151, 153, 155, 191, 213; 623/11.11, 23.65, 23.72; 604/174
See application file for complete search history.

(56) References Cited

U.S. PATENT DOCUMENTS

| | | | |
|---|---|---|---|
| 3,196,876 A * | 7/1965 | Miller | 606/191 |
| 5,116,357 A | 5/1992 | Eberbach | |
| 5,397,331 A | 3/1995 | Himpense et al. | |
| 5,545,178 A | 8/1996 | Kensey et al. | |
| 6,547,806 B1 * | 4/2003 | Ding | 606/213 |
| 2002/0147457 A1 * | 10/2002 | Rousseau | 606/157 |
| 2005/0288787 A1 * | 12/2005 | Crawley et al. | 623/11.11 |
| 2007/0027358 A1 | 2/2007 | Gertner et al. | |

FOREIGN PATENT DOCUMENTS

| | | |
|---|---|---|
| FR | 2872024 | 12/2005 |
| GB | 2397240 | 7/2004 |
| WO | 2006009925 | 1/2006 |

* cited by examiner

*Primary Examiner* — Melanie Tyson
(74) *Attorney, Agent, or Firm* — John L. Rogitz

(57) ABSTRACT

A space in a muscle wall such as the inguinal canal is dilated to break up fibrotic bands by divulsion. While the space is dilated a dynamic plug is advanced into it, with the plug expanding and contracting with the space. Shields may be placed against opposite sides of the wall surrounding the space.

1 Claim, 12 Drawing Sheets

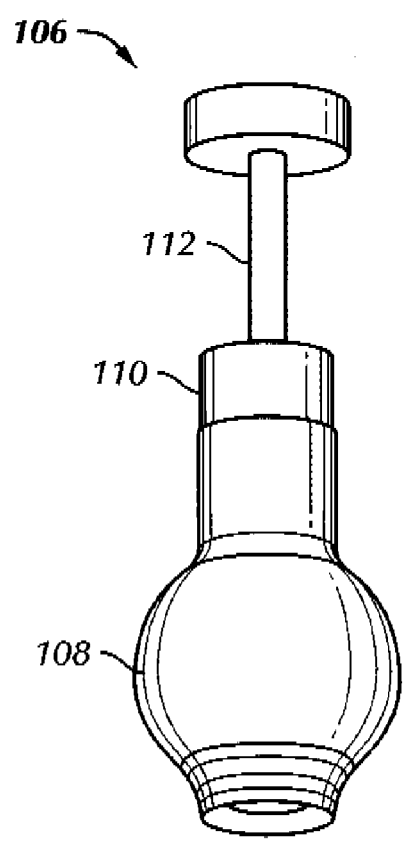
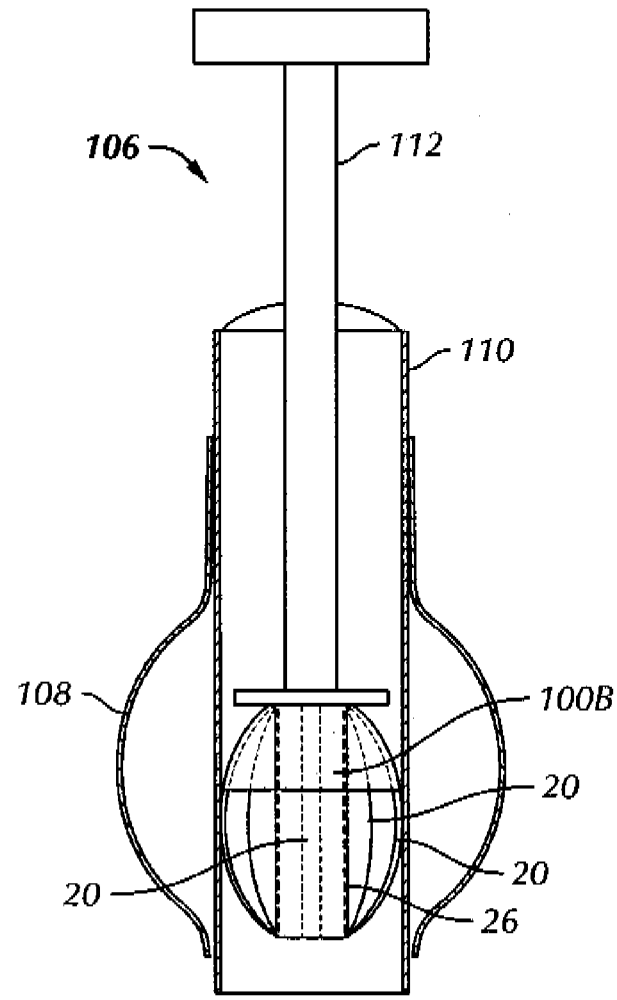
FIG. 11A
FIG. 11B

APPARATUS AND REPAIR OF DEFECT IN INGUINAL CANAL AND OTHER MUSCULAR STRUCTURES

Priority is claimed to U.S. provisional application 60/895,039, filed Mar. 15, 2007.

I. FIELD OF THE INVENTION

The present invention relates generally to the repair of defects in muscular structures, and more particularly to repairing direct and indirect inguinal hernias.

II. BACKGROUND OF THE INVENTION

A hernia is a condition in which part of the intestine bulges through a weak area in muscles of the abdomen. Ai inguinal hernia, the most common of which are the "indirect" and the "direct" inguinal hernia, occurs in the groin area between the abdomen and thigh. In an inguinal hernia the intestines push through a weak spot in the inguinal canal, which is an opening between layers of abdominal muscle near the groin. Obesity, pregnancy, heavy lifting, and straining to pass stool can cause the intestine to push against the inguinal canal. As also recognized herein, other repeated minor trauma to the wall from, e.g., coughing and the like can create the weakness that develops into a hernia.

The main treatment for inguinal hernia is surgery to block the protrusion of abdominal content through the muscle wall. This surgery is called herniorrhaphy, and typically involves suturing the muscle layers and fascia together to reinforce the wall or blocking the defect with a flat polypropylene mesh, and in some procedures used with a static polypropylene plug which rests in the opening without exerting any pressure on the surrounding tissue. As understood herein, this procedure can lead to complications including pain, swelling, bleeding, as well as recurrence.

As critically recognized herein, the inguinal canal is no mere static tube, but rather an active muscular sphincter the mode of failure of which is muscle fibrosis stemming from prolonged inflammation from years of impact with surrounding tissue during, e.g., coughing. Indeed, the present invention recognizes that the mode of failure in many muscular walls in the body such as that of the muscle wall of the groin (whose failure can lead to so-called "direct" hernias), the septum of the heart, etc. is the fibrotic alteration of the muscle's structure. With these critical recognitions in mind, the invention herein is provided.

SUMMARY OF THE INVENTION

An apparatus includes a fibrotic band interrupter juxtaposable with a space surrounded by a muscle wall and operable to break at least one fibrotic band in the wall to at least partially restore contractibility of the muscle wall. An implant is disposable in the space, and the implant is biased to a radially enlarged configuration. The implant assumes a radially contracted configuration when the muscle wall causes the space to contract. The implant assumes the radially enlarged configuration when the muscle wall causes the space to dilate such that the implant remains in contact with the muscle wall surrounding the space, providing a counterpressure expanding motion.

In some embodiments the interrupter can be a dilator that breaks the fibrotic band through divulsion thereof. The dilator may include a tube, with the implant being advanceable along the tube and into the space while the dilator holds the space in a dilated state. A flat wall shield may be disposed against a side of the wall surrounding the space. The wall shield can be a first wall shield, the side can be a first side, and the apparatus may further include a second wall shield disposable against a second side of the wall surrounding the space.

In non-limiting embodiments the implant includes a radially compressible resilient cylindrical member and radial struts that bias the member to the radially enlarged configuration. Or, the implant can include a plurality of bowed loops equidistantly spaced from each other around a core. The implant can include a resilient flexible deploying disc coaxially coupled to an end of the core, with the deploying disc stopping the implant from dislodging and protecting newly repaired muscular structure from recurrent injury related to visceral impact. The deploying disc can be materially biased to a radially enlarged and substantially flat configuration, wherein the diameter of the disc is significantly larger than (on the order of 1.5 times larger than) the diameter of the core, and can be folded into a non-flat, radially small configuration in which substantially the entire disc is closely juxtaposed with the core. The disc may be formed with a slit to permit the spermatic cord to pass through the disc. The slit can be preformed in the disc or formed in situ.

Also, a flat mesh can be disposed on an end of a core of the implant by means of, e.g., a snap fitting.

When the implant includes loops, two loops can be disposed in tandem in the axial dimension of the core, with one end of each loop coupled to a respective end of the core and with the other end of each loop coupled to the core at or near the middle of the core.

In yet another implementation the implant has flexible stabilizing loops extending from one end to the other end of a core. Each stabilizing loop includes a generally radial segment extending radially away from the core at or near one end thereof and a generally axial segment unitarily formed with a respective radial segment and extending generally parallel to the axis of the core. Elongated members forming tandem loops may also be provided, with one axial level of the loops meeting flush with a respective radial segment of a stabilizing loop.

In another non-limiting implementation the implant can include a core radially surrounded by and in axial contact with hollow axially elongated resilient compressible elements. The elements may have circular, ovular, or triangular transverse cross-sections. This geometry avoids compression of biologic structures such as the spermatic cord while leaving space for the cord to slide relative to the implant.

A non-limiting dilator may include a hollow cylinder receiving the implant and an inflatable balloon surrounding the cylinder for movement between a deflated configuration and an inflated configuration in which the balloon dilates a muscle wall surrounding a space in which the cylinder is disposed. A plunger can be slidably disposed within the cylinder, the plunger being operable to urge the implant out of the cylinder into the space. Another embodiment of the dilator includes outer dilation valve flaps surrounding an inner cylinder holding the implant, with the dilation valve flaps being movable toward an outward direction, thereby dilating muscular structure. Yet another dilator embodiment includes a radially enlarged rigid hollow element such as a rigid olive-shaped enlargement on an outer surface of a cylinder.

In another aspect, a method includes breaking at least one fibrotic band juxtaposed with a space in a muscle wall by divulsion induced by dilating the muscle wall. It is to be understood that prior to divulsion, adhesions may be removed. After division of the adhesions, an implant is advanced into the void of muscle wall. The implant exerts a radial force against the portion of the muscle wall surrounding the space when the wall is dilated and when the wall is not dilated. After implant disposition, the wall may be shielded and/or supported.

In still another aspect, an apparatus includes a dilator configured for expanding while disposed in a space surrounded by a muscle wall to dilate the wall, and an implant associated with the dilator and being advanceable into the space. The implant is configured for exerting radially outward pressure on the wall when the wall is dilated and for accommodating contraction of the wall.

The details of the present invention, both as to its structure and operation, can best be understood in reference to the accompanying drawings, in which like reference numerals refer to like parts, and in which:

BRIEF DESCRIPTION OF THE DRAWINGS

FIG. 11A is a perspective view of an applicator according to a further embodiment of the applicator;

FIG. 11B is a cross-sectional view of the applicator shown in FIG. 11A;

DETAILED DESCRIPTION OF THE PREFERRED EMBODIMENT

Figure 1:
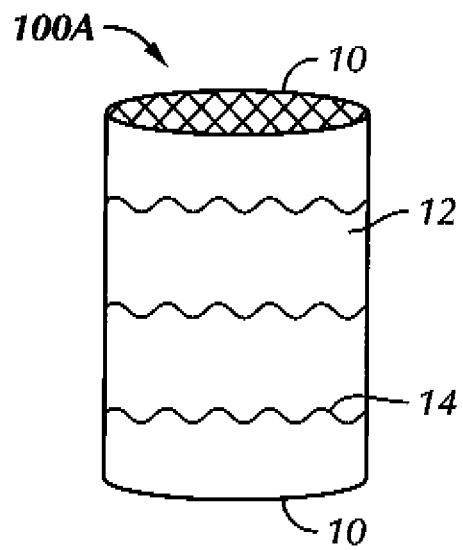
FIG. 1 is a perspective view of an embodiment of a dynamic implant according to one non-limiting embodiment of the present invention which, like the implant-only figures herein, shows the implant in the radially enlarged (materially biased) configuration.

As set forth in greater detail below, methods and devices are disclosed to dilate the muscular gap in which protrudes the hernia, as well as the inguinal canal, indeed in some embodiments the entire inguinal canal, for the purpose of rupturing fibrous bands within the muscle wall to allow a return to the natural physiological state of contraction/relaxation and, thus, blocking and at the same time accomplishing in dynamic fashion the action of the sphincter (or similar anatomical structures that function like a sphincter) even in the case of anterior or posterior open hernia procedure as well as during any appropriate type of laparoscopic approach such as TAPP or TEP. A dilating instrument may be used to dilate the opening for the above purpose. The dilating instrument may be engaged with a preloaded implant and if desired a force gauge mechanism (e.g. manometer) to precisely control the dilation forces. Manual, hydraulic, electrical, electronic, magnetic, mechanical power-drive or other kind of controlled motion may be used to spread out the entire inguinal canal or similar anatomical structures that function like a sphincter.

A dynamic implant is deployed that contracts and relaxes with the inguinal canal. In addition, in non-limiting embodiments adhesions may be resolved to further release the muscle wall prior to dilation by, e.g., scrubbing the adhesions with a pad. When the delivery device is removed the newly restored contractibility of the muscle usually causes the muscle to grasp and hold the implant.

In addition to physical dilation of the defect, the fibrous bands can also be disrupted using mechanical, electrical, thermal, magnetic, or chemical processes. For example, direct or indirect stimulation by electricity of the muscles can be used to create deform spasms which through non-physiologic contraction break the fibrosis. Cooling or beating may be used at temperatures established to break the stiff connective fibers only within the muscles, thus breaking the fibrosis. Magnetic objects such as small magnetic or ferromagnetic discs or even small particles can be disposed in the inguinal ring through, e.g., a catheter and then a large magnet disposed external to the patient to attract the internal magnetic objects to stretch the muscles and cause divulsion. Enzymatic or chemical lysis of stiff connective fibers can be applied through, e.g., hypodermic injection or preoperatively to break down only fibrotic tissue and not healthy tissue.

As described further below, the present implant preferably is a dynamic device that expands and contracts in a radial fashion in synchrony with the muscles of the entire inguinal canal to allow the contraction and relaxation of the sphincter in a normal physiological way. The implant is configured to exert a constant outward pressure on the surrounding tissue, and it may incorporate a unique lamellar structure at its core to allow the spermatic cord to slide freely along the length of the core, thus not impinging the cord structures and vessels. The implant may be made of materials that have low tissue reactivity. A solid, liquid gel or gas or combination of any to create the implant and can be made from autologous tissues, xenotissues or any form of biological material. The implant can be permanent, temporary, absorbable, non-absorbable or a combination of all of these and can be detected radiologically or by using other imaging diagnostic procedures. The implant can be, e.g., tubular, round, conical, irregular, regular etc. The implant may be retained within the defect by friction, i.e., by radial force between the implant and muscle wall. Also, the implant may sutured, clipped, or glued to the wall.

Application of the implant may use open abdomen surgery, laparoscopic surgery, endoscopic surgery, or a combination thereof. The implant can be deployed forwards or backwards, and the applicator can be temporary, permanent, non-absorbable, or absorbable.

Referring to FIG. 1, a first embodiment of an implant 100A includes a radially compressible resilient cylindrical member 12 the ends of which may be covered with discs 10. The member 12 also includes radial struts 14 that bias the member 12 to the relatively radially enlarged configuration shown. Like the other implants disclosed herein and as set forth in greater detail below, the implant 100A assumes a contracted radial configuration when the muscle wall surrounding the location in which the implant 100A is disposed causes the space to contract. And, the implant assumes the enlarged radial configuration when the muscle wall causes the space to dilate such that the implant 100A remains in contact with the muscle wall surrounding the space. The implant can be hollow if desired and can be formed with a slit on the side to permit passage of the spermatic cord when the implant is used in the inguinal canal.

Figure 2:
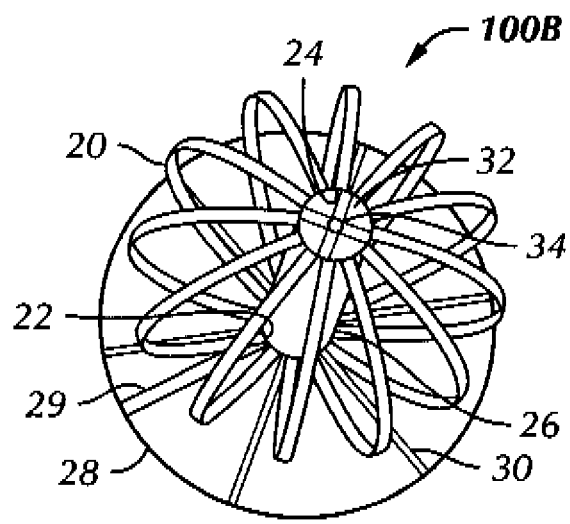
FIG. 2 is a perspective view of another embodiment of dynamic implant.

An alternate implant 100B is shown in FIG. 2. The implant 100B includes a plurality of bowed loops 20 having rectilinear transverse-cross-sections. The loops 20 which are radially equidistantly spaced from each other and which surround the core, are formed from flexible members arranged and constructed to form loops 20. The members extend from one end 22 to the opposite end 24 of a hollow or solid core member 26 that may have a cylindrical outer surface as shown. Because the preferred loops 20 radially surround the core member 26, together they establish a resilient compressible member of generally spherical shape as shown.

It may be readily appreciated that the cylindrical surface of the core member 26 restricts inward motion (contraction) of the loops 20 while the engagement between the ends of the core member 26 and the ends of the loops 20 restrict outward motion (expansion) of the member in a radial direction. It may be further appreciated that the member established by the loops 20 is materially biased into the enlarged radial configuration shown, and that when the member is disposed in a defect in a muscle wall or other space such as the inguinal canal and the space contracts, the member can be compressibly deformed into a radially smaller configuration, owing to the flexibility of the loops 20. When the member is released, owing to its resiliency it assumes the radially enlarged configuration.

Additionally, a resilient flexible deploying disc 28 may be coaxially coupled to one end of the core member 26. The deploying disc 28 is provided for stopping the implant from dislodging and for protecting the newly repaired muscular structure from recurrent injury related to visceral impact. The disc can be round as shown, or it can be oval or any other geometric shape that allows the deployment and function as described above. The disc 28 can be formed with an optional opening or slit 29 to permit the spermatic cord to pass through the disc and between adjacent loops 20. The slit may be lined with a closure such as Velcro to hold it closed.

In accordance with the embodiment shown in FIG. 2, the deploying disc 28 is materially biased to the radially enlarged and substantially flat configuration shown, wherein the diameter of the disc 28 is significantly larger than the diameter of the core 26 and may be larger than the diameter of the loop member when the loop member is in the enlarged configuration, so that the diameter of the disc 28 is greater than the diameter of the defect or space sought to be resolved. When deployed, the disc establishes a shield. Because it is flexible, the deploying disc 28 can be folded into a non-flat, radially small configuration in which the entire disc 28 is closely juxtaposed with the core 26, i.e., the disc 28 can be folded against the core 26 by, e.g., advancing the core 26, disc 28 first, into an introducer tube to cause the disc 28 to fold against the core. Then, the introducer tube can be advanced through the defect or space sought to be resolved and the core 26 pushed further into the tube, causing the disc 28 to emerge from the tube at the far side of the muscle wall. When the disc 28 emerges from the tube, owing to its material bias it assumes the enlarged, flat configuration shown in FIG. 2.

If desired, flexible resilient elongated spokes 30 can extend from the core 26 to the outer periphery of the disc 28. The spokes 30 are materially biased to the elongated configuration shown, and like the disc 28 can be folded against the core 26. The spokes 30 provide additional strength to the deploying disc 28 and help to unfold the deploying disc during implantation of the implant. In some implementations the spokes may assume a spiral shape when unfolded. The spokes or spiral may also be biased towards the core 26, so that the disk 28 has a convex shape.

As described further below, a flat metal or polypropylene mesh or other shield can be disposed on the near end of the core 26, i.e., on the end opposite that which is coupled to the disc 28. To this end, in some implementations an orifice plug 32 can be inserted into the near end of the core 26, with the plug 32 defining an orifice 34. The below-described mesh can be positioned against the end of the core 26 after disposing the flexible member in the inguinal canal or muscular defect with the disc 28 deployed on the opposite side, and a fastener then engaged with the mesh and advanced into the orifice 34 in an interference fit to hold the mesh onto the core 26, flat against the near wall of the muscle to function as a shield and reinforcement. Desirably, dimensionally, the flat mesh is larger than the defect sought to be resolved to reinforce the muscle wall, particularly but not exclusively in the case of mixed hernias or wide inguinoscrotal hernias.

Figure 3:
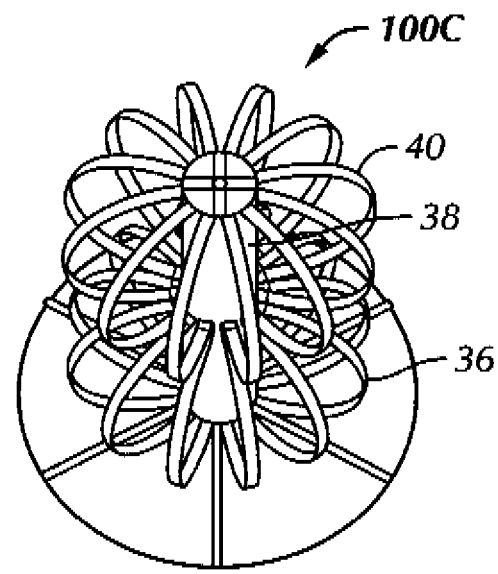
FIG. 3 is a perspective view of yet another embodiment of dynamic implant.

Yet another embodiment 100C of the dynamic implant is shown in FIG. 3, which in all essential respects is identical to that shown in FIG. 2 with the following exceptions. The implant 100C of FIG. 3 includes a resilient compressible member made of elongated curved members 36 extending from one end to another end of a core member 38. As shown, each elongated member 36 forms two loops 40 that are disposed in tandem in the axial dimension of the core, with one end of each loop coupled to a respective end of the core and with the other end of each loop coupled to the core at or near the middle of the core as shown.

Figure 4:
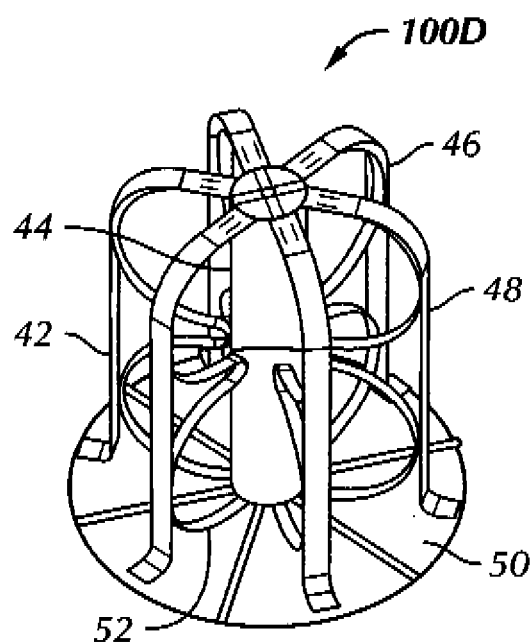
FIG. 4 is a perspective view of further embodiment of dynamic implant.

Yet another embodiment 100D of the dynamic implant is shown in FIG. 4, which in all essential respects is identical to that shown in FIG. 3 with the following exceptions. The implant 100D of FIG. 4 includes flexible stabilizing loops 42 extending from one end to the other end of a core member 44. Each stabilizing loop 42 includes a generally radial segment extending radially away from the core 44 at or near one end thereof and a generally axial segment 48 unitarily formed with its respective radial segment 46 and extending generally parallel to the axis of the core 44 to a disc 50 coupled to the opposite end of the core 44 as shown.

In addition, the implant 100D can include elongated members 52 that form double (tandem) loops as described above in reference to FIG. 3, with one axial level of the loops meeting flush with a respective radial segment 36 of a stabilizing loop 42 as shown. The stabilizing loops 42 reinforce and further stabilize the loops of the implant 100D.

Figure 5:
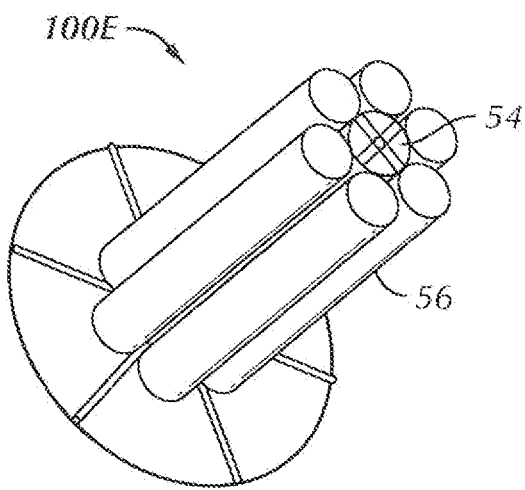
FIG. 5 is a perspective view of another embodiment of dynamic implant.

FIG. 5 shows an implant 100E that includes a core 54 radially surrounded by and in axial contact with hollow axially elongated cylindrical resilient compressible elements 56. Each element 56 may be made of flexible fabric or plastic (or the combination of flexible fabric and more resilient plastic or metal supports) that is rendered into the cylindrical configuration shown.

Figure 6:
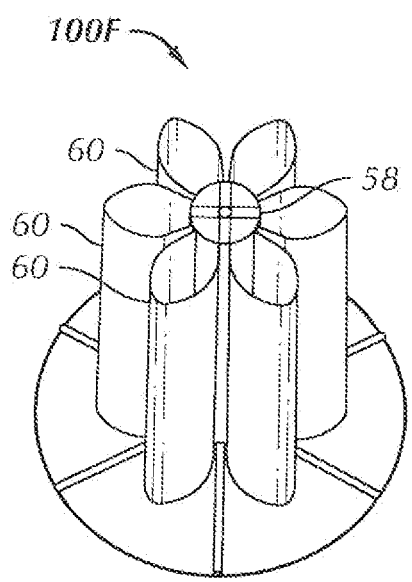
FIG. 6 is a perspective view of another embodiment of dynamic implant.

FIG. 6 shows an implant 100F that is in all essential respects identical to the implant 100E shown in FIG. 5, except that instead of a core 58 that is radially surrounded by and in axial contact with resilient compressible elements having circular transverse cross-sections, the core 58 is radially surrounded by and in axial contact with resilient axially elongated hollow compressible elements 60 having ovular transverse cross-sections.

Figure 7:
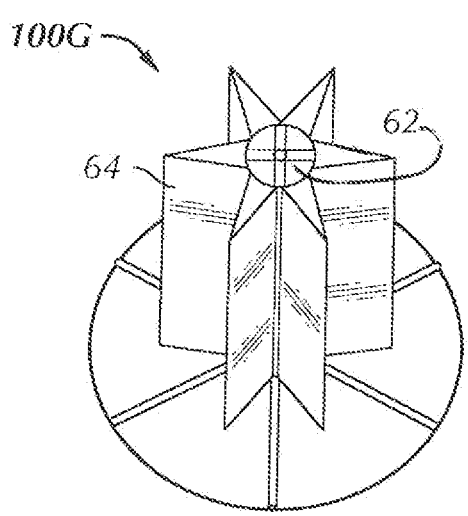
FIG. 7 is a perspective view of another embodiment of dynamic implant.

FIG. 7 shows an implant 100G that is in all essential respects identical to the implant 100E shown in FIG. 5, except that instead of a core 62 that is radially surrounded by and in axial contact with resilient compressible elements having circular transverse cross-sections, the core 62 is radially surrounded by and in axial contact with resilient axially elongated hollow compressible elements 64 having triangular transverse cross-sections.

Figure 8A:
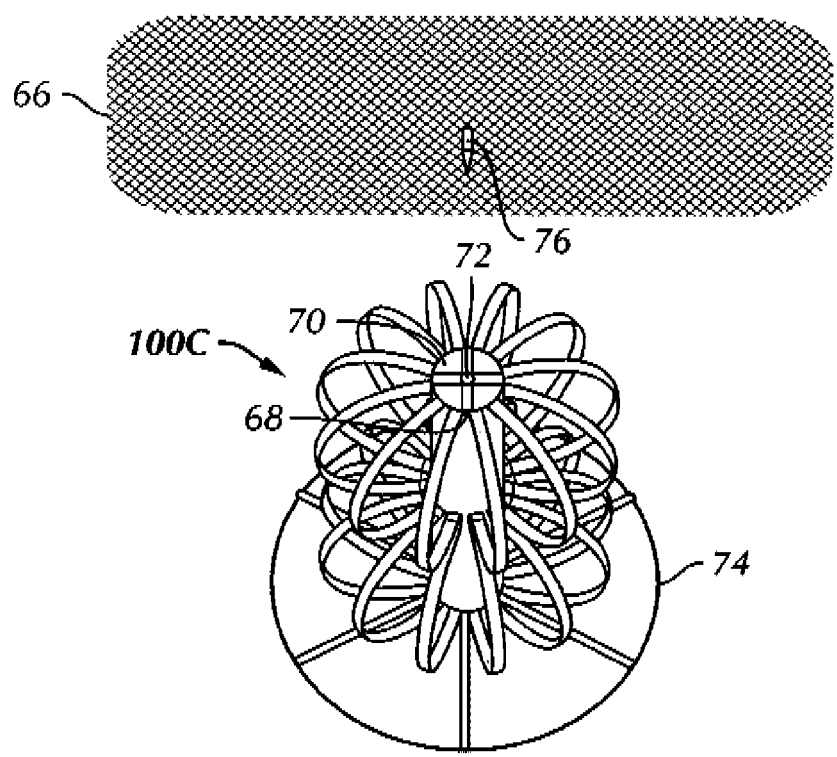
FIGS. 8A and 8B illustrate fixing of a mesh over the implant.
Figure 8B:
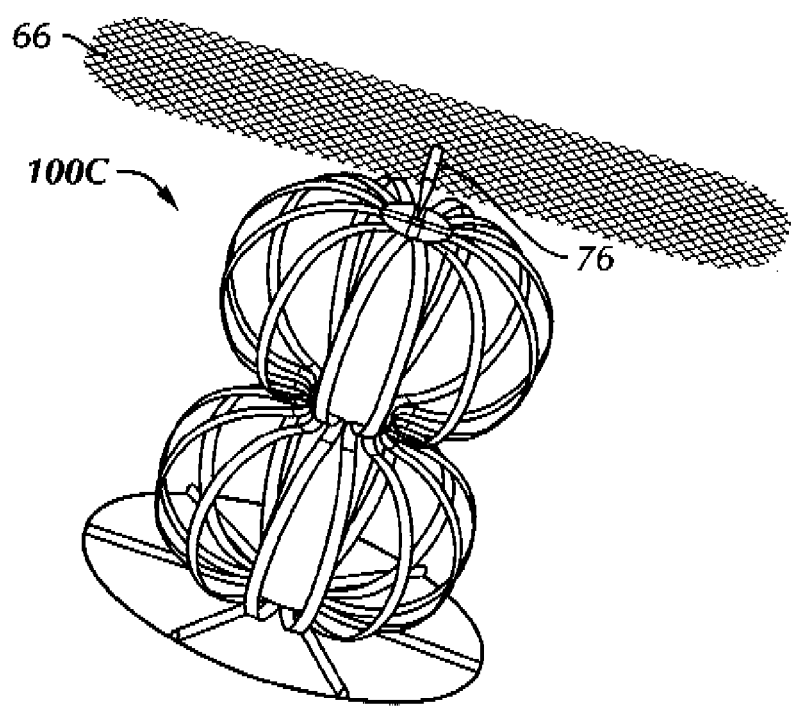

FIGS. 8A and 8B illustrate, using the implant 100C shown in FIG. 3 as a non-limiting example, how a flat fabric or polypropylene mesh 66 or other shield can be disposed on an end 68 of the core 38. To this end, in some implementations an orifice plug 70 can be inserted into the end of the core 38, with the plug 70 defining an orifice 72. The mesh 66 can be positioned against the end of the core 38 after disposing the flexible member 74 in the intended space with the disc 74 deployed, and a fastener such as a pin 76 then engaged with the mesh and advanced into the orifice 72 in an interference fit to hold the mesh onto the core, flat against the outer wall of the muscle to function as a support. Desirably, dimensionally the flat mesh is larger than the defect sought to be resolved to reinforce the muscle wall, particularly in the case of mixed hernias or wide inguinoscrotal hernias. In a further embodiment the mesh can be attached to the core by means of an adjustable post or strap so that the distance from the flexible member 74 to the mesh 66 can be reduced to accommodate variations in patient anatomy.

According to the present invention, the implant can be deployed by using an applicator of the present invention, which includes structure to dilate the muscular structure to break fibrotic bands between and within the muscle wall or inguinal canal or other muscle wall, and structure to deploy the implant within the intended space.

Figure 9A:
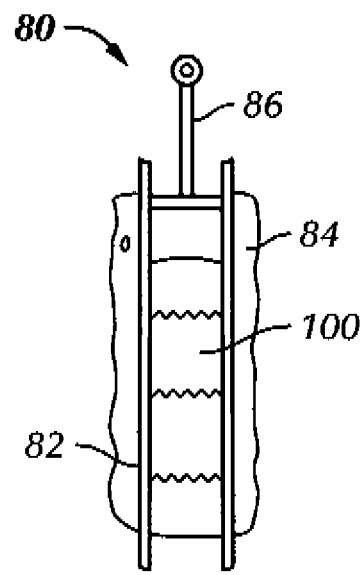
FIGS. 9A and 9B are perspective views of an applicator according to one embodiment.
Figure 9B:
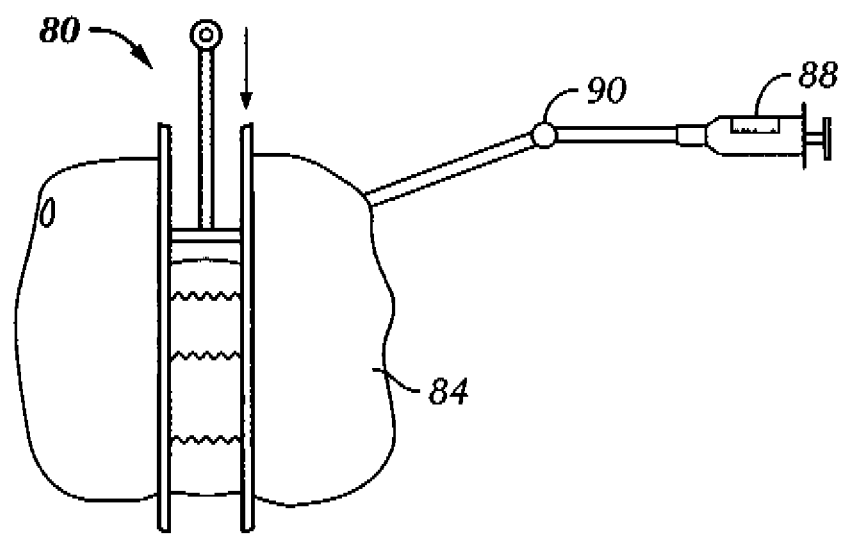

One non-limiting embodiment is shown in FIGS. 9A and 9B. An applicator 80 includes a hollow cylinder 82 to receive an implant of the present invention, such as but not limited to the implant 100, in the radially compressed configuration, with the deploying disc (omitted for ease of disclosure in FIGS. 9A and 9B) in a folded configuration.

An inflatable balloon 84 surrounds the cylinder 82 and can be attached thereto for movement between a deflated configuration (FIG. 9A) and an inflated configuration (FIG. 9B), in which the balloon 84 dilates the muscle wall surrounding the space into which the cylinder has been advanced. A plunger 86 is slidably disposed within the cylinder 82. After positioning the distal segment of the cylinder 82 within the desired space and inflating the balloon to effect divulgation of the surrounding muscle wall, a surgeon can push the plunger to urge the implant 100 out of the cylinder 82 into the desired space. As the implant clears the cylinder 82 it assumes the radially enlarged configuration within the dilated structure. The balloon may then be deflated and the cylinder withdrawn, leaving the implant in the desired space to strengthen it (particularly in the case of the inguinal canal) and/or to block the space (in the event that the space is a hole in a muscle wall sought to be resolved).

FIG. 9B illustrates that the balloon 84 may be inflated by using known means such as fluid or gas from a syringe 88 or other source which may be connected to the balloon through a relief valve 90 that is external to the patient. The relief valve 90 opens at a predetermined pressure to prevent overpressurization, hence protecting the tissues from overstretching and subsequent damage. The aim of the applicator is to break the fibrotic bands but not damage the muscular structure itself.

Figure 10A:
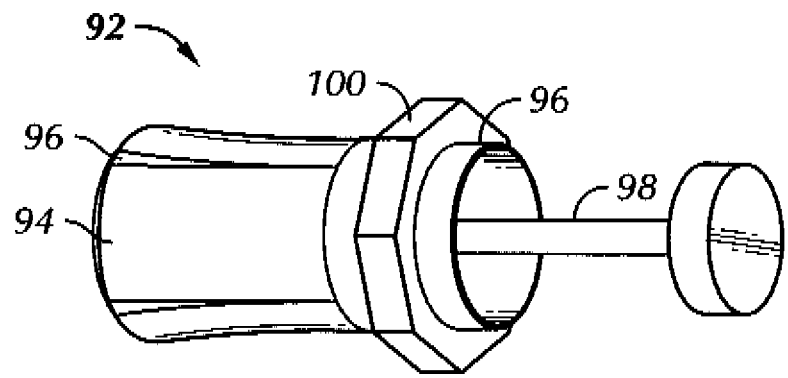
FIG. 10A is a perspective view of an applicator according to a further embodiment of the applicator.
Figure 10B:
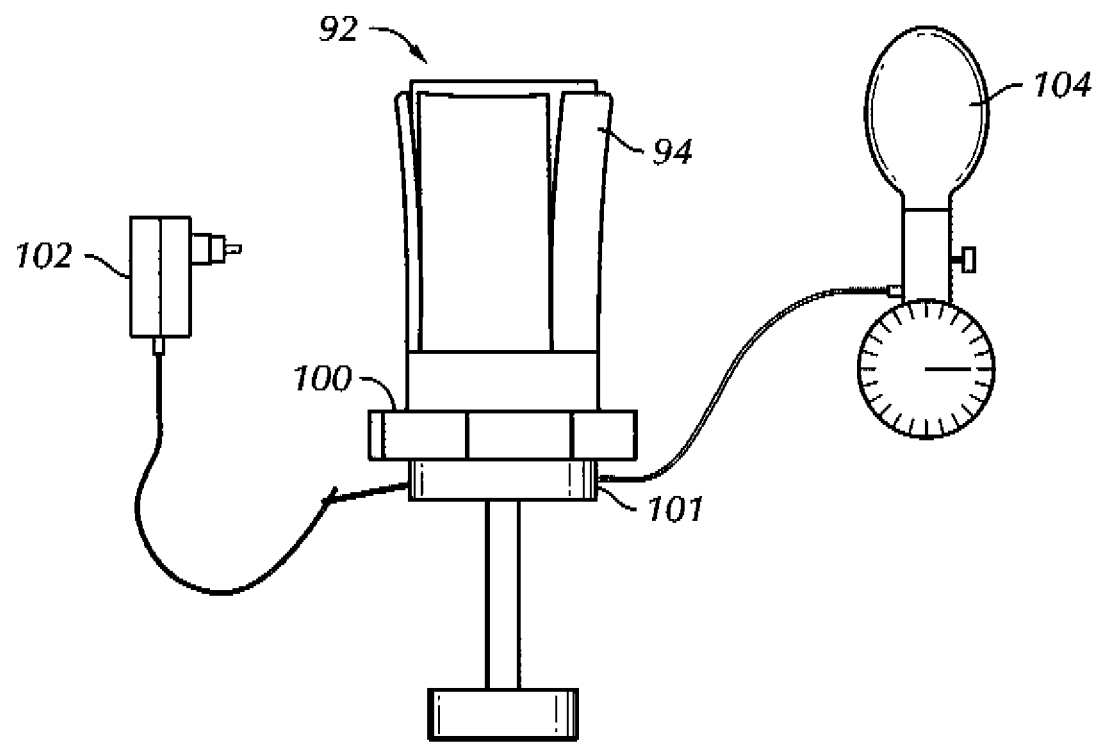
FIG. 10B is a perspective view of the applicator with different possible embodiments according to the present invention.

Another embodiment of the applicator is shown in FIGS. 10A and 10B. The applicator 92 includes outer dilation valve flaps 94, an inner cylinder 96 which holds the implant, and a plunger 98 slidably disposed in the inner cylinder 96. A rotation knob 100 is rotationally connected the dilation valves 94 and can be rotated to move the dilation valves 94 in an outward direction, thereby dilating the muscular structure.

As shown in FIG. 10B, the rotation knob 100 can be operated electrically to open the dilation valves. More specifically, an electric motor 101 can be coupled to the knob 100 to rotate it, with the motor being powered from an electrical source 102. The motor can have a channel for receiving the plunger therethrough. If desired, the pressure applied by the dilation valves 94 on the muscular structure can be measured with a pressure sensor such as a manometer 104, which can, e.g., sense torque on the knob 100, to control opening of the dilation valves by means of feedback to the knob motor.

In one non-limiting implementation, each valve flap is a concave bow, with its midpoint pivotably resting on the surface of the inner cylinder. Small camming surfaces, one surface for each valve flap, are formed on the inside surface of the knob, and the end of the respective valve flap is disposed between its camming surface and the cylinder. Accordingly, when the knob turns the camming surface rides against the end of its valve flap, pushing it toward the cylinder. The valve flap rocks on its midpoint, causing the opposite (far) end of the valve flap to deflect outwardly. Since all the valve flaps deflect in synchrony around the complete circumference of the applicator, the space in which the far (outwardly deflecting) ends of the valve flaps are positioned is dilated.

FIGS. 11A and 11B show that an applicator 106 can dilate the muscular structure using an ovular-shaped rigid hollow olive 108 provided on an outer surface at the deploying end of a cylinder 110. A plunger 112 may be slidably disposed in the cylinder 110 to deploy an implant such as the implant 100B shown in FIG. 2 during dilation in accordance with the above principles. The olive 108 may have any suitable shape for dilation such as frusto-conical shape tapering towards the deploying end.

FIGS. 12A-12D illustrate principles discussed above. After removal of adhesions, e.g., that might exist between the hernia sac and the muscular structure and using the applicator 80 shown in FIG. 9 as a non-limiting example, the balloon 84 is advanced into the desired space in the muscular structure while in the deflated configuration (FIG. 12A), and then inflated FIG. 12B) to dilate the muscular structure, thereby effecting divulsion of the fibrotic bands to restore the contractibility of the muscle. Then, the preloaded compressed dynamic implant in the cylinder is introduced within the desired space and the applicator removed in accordance with above principles.

Figure 12A:
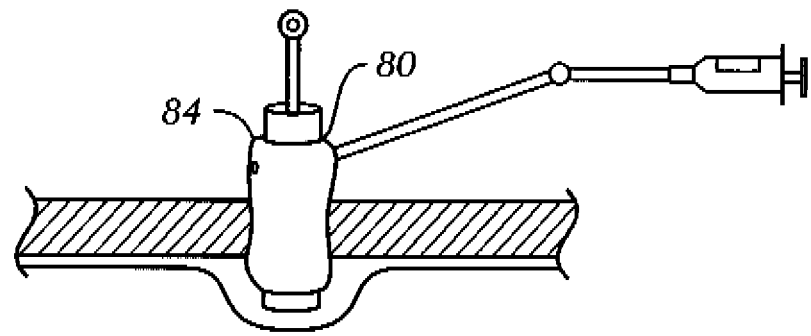
FIGS. 12A-12D are views illustrating non-limiting steps of a method of the present invention using the applicator as shown in FIGS. 9A and 9B.
Figure 12B:
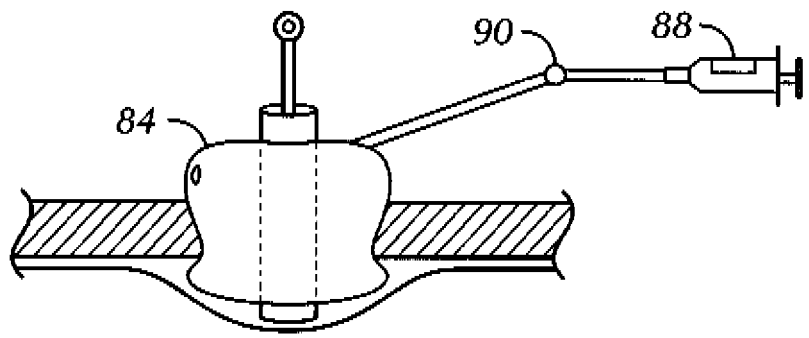
Figure 12C:
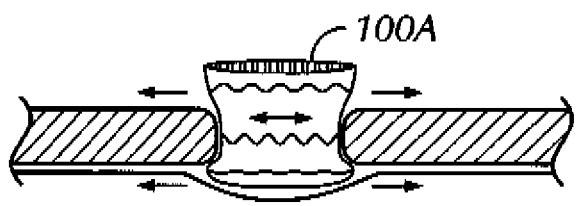

As shown in FIG. 12C, the dynamic implant (using the implant 100A as a non-limiting example) upon introduction within the space assumes the radially enlarged configuration owing to the dilation of the surrounding muscle wall, abutting the surrounding wall substantially completely around the periphery of the space. Because the dynamic implant of the present invention is biased to the enlarged configuration in which the diameter of the implant is substantially equal to or larger than the diameter of the space when the muscle is dilated as intended, the implant exerts a radial force on the surrounding muscle wall, thereby self retaining in the space.

Figure 12D:
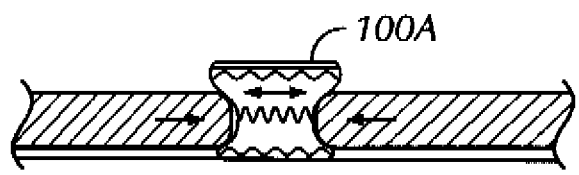

Further, owing to its resiliency the dynamic implant contracts and expands in synchrony with the contracting muscular structure as indicated by the arrows in FIGS. 12C and 12D, thereby reinforcing the surrounding muscle wall. Specifically, when the muscle wall contracts it urges the implant to the radially smaller configuration as shown in FIG. 12D.

Figure 13A:
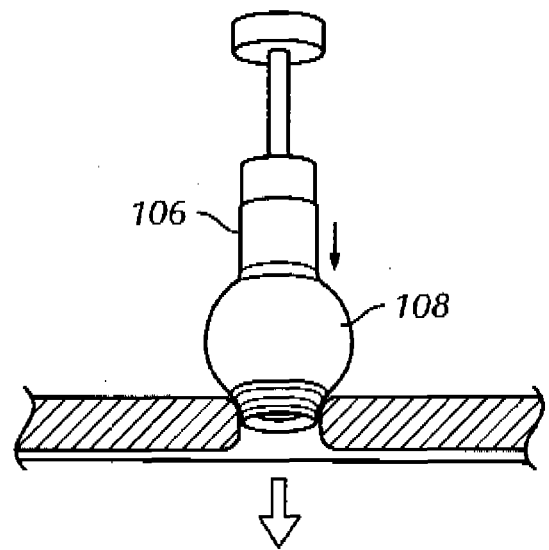
FIGS. 13A-13C are views illustrating non-limiting steps of a method of the present invention using the applicator as shown in FIGS. 11A and 11B.
Figure 13B:
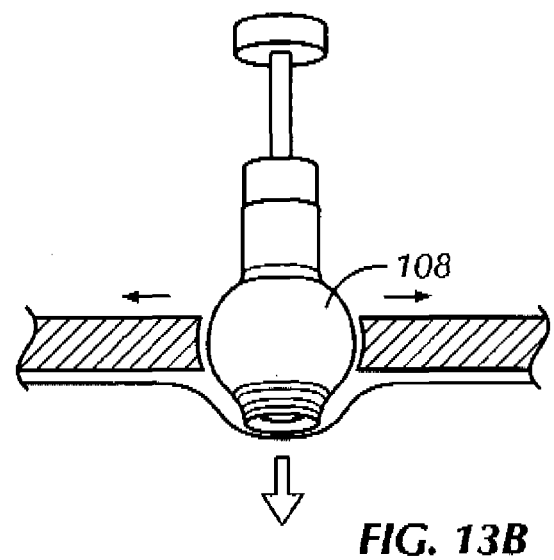
Figure 13C:
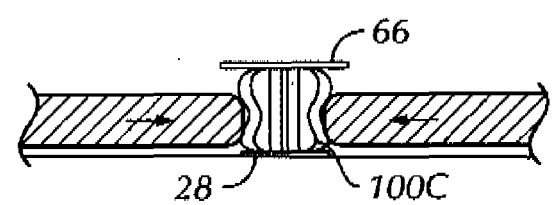

FIGS. 13A-13C illustrate how the applicator 106 shown in FIG. 11 can be used. In FIG. 13A, the olive 108 is advanced into the desired space to dilate it as shown in FIG. 13B. It is then retracted and an implant such as the implant 100B shown in FIG. 3 is pushed out of the applicator into the space, with the disc 28 unfolding against one side of the muscle wall as shown and the mesh 66 engaged with the opposite end of the implant against the opposite surface of the muscle wall as shown and discussed above.

FIGS. 14A through 14E show the use of the applicator 92 shown in FIGS. 10A and 10B to deploy an implant such as the implant 100B shown in FIG. 2. FIGS. 14A-14E assume repair and reinforcement of the muscular structure surrounding an inguinal hernia which has formed at the level of the spermatic cord.

Figure 14A:
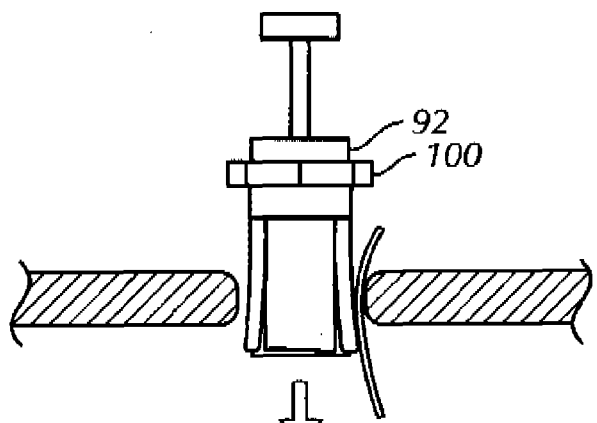
FIGS. 14A-14E are views illustrating non-limiting steps of a method of the present invention using the applicator as shown in FIGS. 10A and 10B.
Figure 14B:
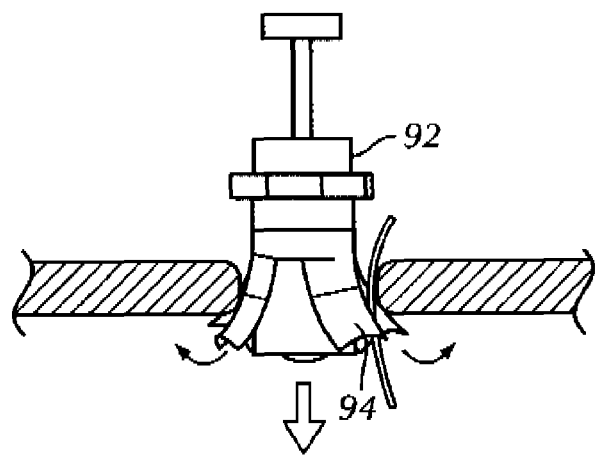
Figure 14C:
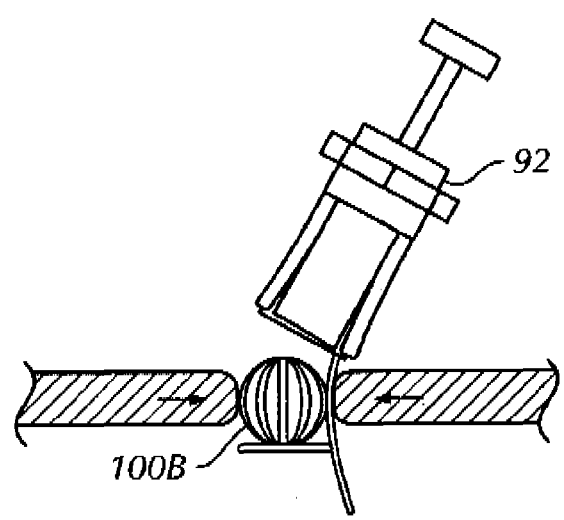
Figure 14D:
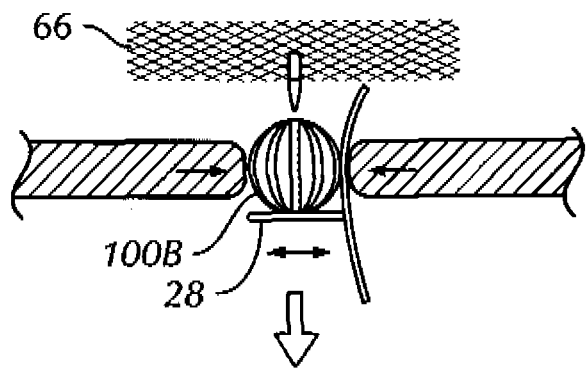
Figure 14E:
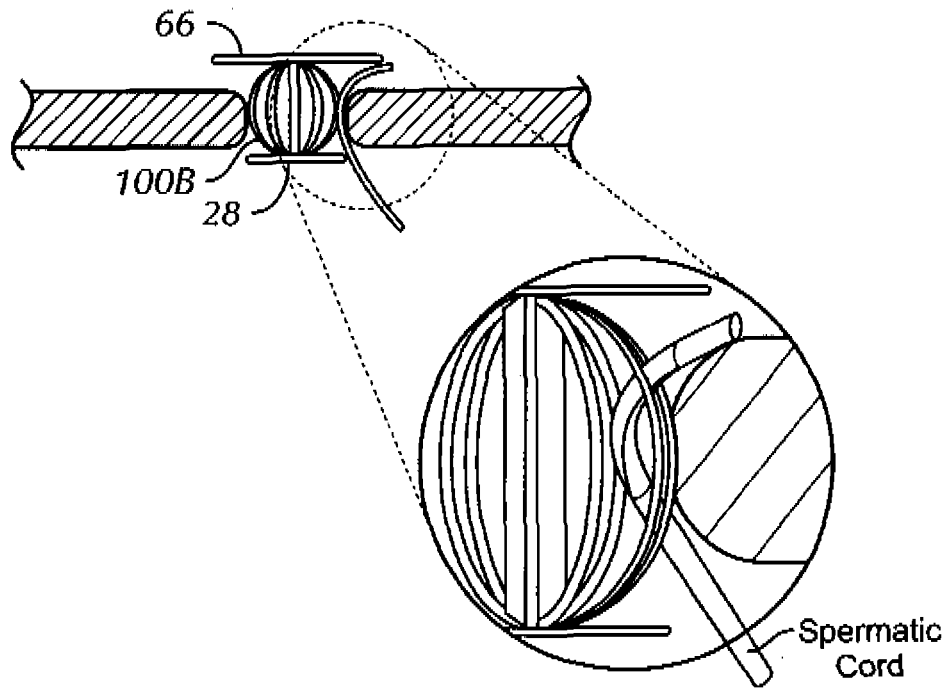

As shown in FIG. 14A, the applicator 92 is introduced in the defect and then the rotation knob 100 rotated to open the dilation valves 94 as shown in FIG. 14B. As shown in FIG. 14C, the implant 100B is then pushed out of the applicator 92 into the defect) to dynamically engage (expand with and contract with) the surrounding muscle walls. FIGS. 14D and 14E illustrate deployment of the opposed shields, e.g., the disc 28 and mesh 66. The loops of the implant 100B and slit in the disc 28 accommodate the spermatic chord structure by allowing it to slide freely along the length of the core.

The dynamic implant, device and/or the method for repairing and reinforcing tissue or muscular structures, according to the present invention can be used to repair all types of hernias including inguinal direct, indirect or mixed hernias, femoral, incisional, and recurrent hernias. The described method may be applicable to other similar muscular wall defects such as trans-septal cardiovascular defects. The scope of the methods of the invention are not restricted solely to hernia but include any body structure requiring divulsion of the surrounding muscular structures to restore contractibility followed by the deployment of an implant with the intention to reinforce the muscular structure allowing a dynamic repair of the physiological functions of the structures.

To use electrical interruption of fibrotic tissue, a tube can be advanced to the site sought to be treated and an electrical device such as a radio frequency probe or microelectrodes advanced out of the tube to the site and activated. The amount of electrical energy is modulated as appropriate to effect the desired disruption without unduly damaging healthy tissue.

To use thermal interruption of fibrotic tissue, a tube can be advanced to the site sought to be treated and a thermal device such as an electrocautery probe advanced out of the tube to the site and activated. The amount of thermal energy is modulated as appropriate to effect the desired disruption without unduly damaging healthy tissue.

To use ultrasonic interruption of fibrotic tissue, a tube can be advanced to the site sought to be treated and an ultrasonic probe advanced out of the tube to the site and activated. The amount of ultrasonic energy is modulated as appropriate to effect the desired disruption without unduly damaging healthy tissue.

To use magnetic interruption of fibrotic tissue, a tube can be advanced to the site sought to be treated and a magnetic device such as an electromagnetic probe advanced out of the tube to the site and activated. The amount of magnetic energy is modulated as appropriate to effect the desired disruption without unduly damaging healthy tissue.

Other muscle walls with defects that may be treated using the systems and methods herein include the septum of the heart, anterior abdominal wall, diaphragm, female pelvic muscles such as levator ani, and the femoral canal.

Figure 15:
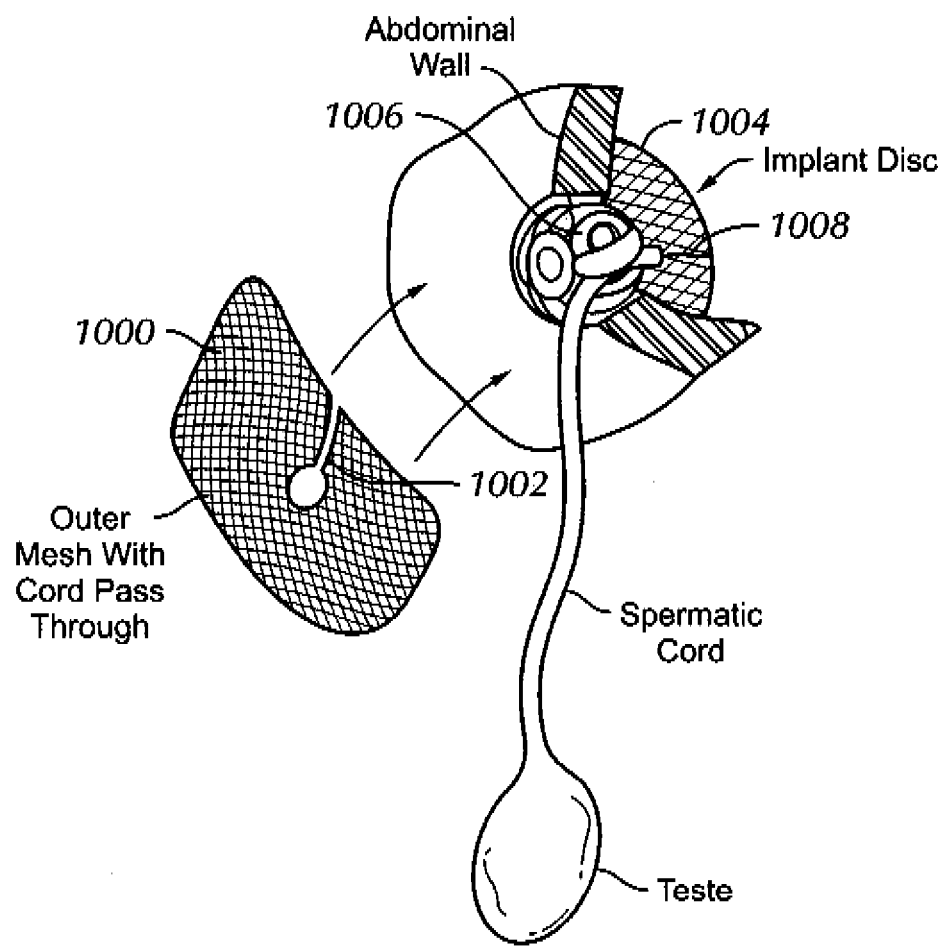
FIG. 15 is a perspective view showing a slitted mesh in an exploded relationship with an implant and slitted disc to accommodate the spermatic cord.

FIG. 15 shows that a mesh 1000 can be formed with a slit 1002 and a disc 1004 opposed to the mesh 1000 across an implant 1006 can also be formed with a slit 1008, to accommodate passage of the spermatic cord through the slits 1002, 1008 and implant 1006 as shown.

While the particular REPAIR OF HERNIA IN INGUINAL CANAL AND OTHER MUSCULAR STRUCTURES is herein shown and described in detail, it is to be understood that the subject matter which is encompassed by the present invention is limited only by the claims.

What is claimed is:
1. Apparatus comprising:
a fibrotic band interrupter juxtaposable with a space surrounded by a muscle wall and operable to break at least one fibrotic band in the wall to at least partially restore contractibility of the muscle wall, an ovular-shaped rigid hollow olive being provided on an outer surface at a deploying end of the interrupter, a plunger being slidably disposed in the interrupter to deploy an implant during dilation; and
at least one implant disposable in the space and slidably engageable with the interrupter, the implant being biased to a radially enlarged configuration, the implant assuming a radially contracted configuration when the muscle wall causes the space to contract, the implant assuming the radially enlarged configuration when the muscle wall causes the space to dilate such that the implant remains in contact with the muscle wall surrounding the space.

* * * * *